(12) United States Patent
Tuval et al.

(10) Patent No.: US 10,856,970 B2
(45) Date of Patent: Dec. 8, 2020

(54) PROSTHETIC HEART VALVE FOR TRANSFEMORAL DELIVERY

(75) Inventors: Yossi Tuval, Even Yehuda (IL); Igor Kovalsky, Givataim (IL); Eli Ben Hamou, Tel Aviv (IL)

(73) Assignee: MEDTRONIC VENTOR TECHNOLOGIES LTD., Netanya (IL)

( * ) Notice: Subject to any disclaimer, the term of this patent is extended or adjusted under 35 U.S.C. 154(b) by 2669 days.

(21) Appl. No.: 12/556,368

(22) Filed: Sep. 9, 2009

(65) Prior Publication Data

US 2010/0268332 A1 Oct. 21, 2010

Related U.S. Application Data

(63) Continuation-in-part of application No. 12/248,776, filed on Oct. 9, 2008.

(60) Provisional application No. 60/978,794, filed on Oct. 10, 2007, provisional application No. 61/192,199, filed on Sep. 15, 2008.

(51) Int. Cl.
*A61F 2/24* (2006.01)

(52) U.S. Cl.
CPC .......... *A61F 2/2418* (2013.01); *A61F 2/2433* (2013.01); *A61F 2/2436* (2013.01); *A61F 2230/005* (2013.01); *A61F 2230/008* (2013.01); *A61F 2230/0013* (2013.01); *A61F 2230/0054* (2013.01)

(58) Field of Classification Search
CPC ..................................... A61F 2/82; A61F 2/24
USPC ....................................................... 623/2.17
See application file for complete search history.

(56) References Cited

U.S. PATENT DOCUMENTS

| | | |
|---|---|---|
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,665,906 A | 5/1987 | Jervis |

(Continued)

FOREIGN PATENT DOCUMENTS

| | | |
|---|---|---|
| CN | 2007-100074433 | 8/2007 |
| DE | 3640745 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Matthew W Schall

(57) ABSTRACT

A prosthetic heart valve capable of being delivered via a transfemoral route as described.

9 Claims, 16 Drawing Sheets

(56) References Cited

U.S. PATENT DOCUMENTS

| | | |
|---|---|---|
| 4,681,908 A | 7/1987 | Broderick et al. |
| 4,710,192 A | 12/1987 | Liotta et al. |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Baykut |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,037,434 A | 8/1991 | Lane |
| 5,047,041 A | 9/1991 | Samuels |
| 5,059,177 A | 10/1991 | Towne et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,217,483 A | 7/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,861,028 A | 1/1999 | Angell |
| 5,876,448 A | 3/1999 | Thompson et al. |
| 5,891,191 A | 4/1999 | Stinson |
| 5,906,619 A | 5/1999 | Olson et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,104 A | 4/2000 | Jang |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,258,114 B1 | 7/2001 | Konya et al. |
| 6,258,120 B1 | 7/2001 | McKenzie et al. |
| 6,277,555 B1 | 8/2001 | Duran et al. |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |

(56) References Cited

U.S. PATENT DOCUMENTS

| | | |
|---|---|---|
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,547,322 B2 | 6/2009 | Sarac et al. |
| 7,556,646 B2 | 7/2009 | Yang et al. |
| 7,806,919 B2 | 10/2010 | Bloom et al. |
| 2001/0002445 A1 | 3/2001 | Vesely |
| 2001/0001314 A1 | 5/2001 | Davison et al. |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Bonhoeffer et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |

(56) References Cited

U.S. PATENT DOCUMENTS

| | | |
|---|---|---|
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Sequin et al. |
| 2004/0093075 A1 | 5/2004 | Kuehn |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143807 A1 | 6/2005 | Pavcnik et al. |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoefer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Case et al. |
| 2007/0027518 A1 | 2/2007 | Herrmann et al. |
| 2007/0027533 A1 | 2/2007 | Douk |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |

(56) References Cited

U.S. PATENT DOCUMENTS

| | | |
|---|---|---|
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065001 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSeggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2009/0287296 A1 | 11/2009 | Manasse |
| 2010/0036479 A1 | 2/2010 | Hill et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 1057460 A1 | 6/2000 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 815 | 4/2002 |
| DE | 1255510 | 11/2002 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 04/019825 | 3/2004 |
| WO | 04/089250 | 10/2004 |
| WO | 05/004753 | 1/2005 |
| WO | 05/046528 | 5/2005 |
| WO | 06/026371 | 3/2006 |
| WO | 08/047354 | 4/2008 |
| WO | 08/138584 | 11/2008 |
| WO | 08/150529 | 12/2008 |
| WO | 09/002548 | 12/2008 |
| WO | 09/029199 | 3/2009 |
| WO | 09/042196 | 4/2009 |
| WO | 09/045338 | 4/2009 |
| WO | 09/061389 | 5/2009 |
| WO | 09/091509 | 7/2009 |
| WO | 09/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.

(56) References Cited

OTHER PUBLICATIONS

Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal 22, Sep. 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.
Cribier, A. et al, "Percutaneous Transcatheter Implantation of an Aortic Valve Prosthesis for Calcific Aortic Stenosis: First Human Case Description," Circulation (2002) 3006-3008.
Davidson et al., "Percutaneous therapies for valvular heart disease," Cardiovascular Pathology 15 (2006) 123-129.
Hanzel, et al., "Complications of percutaneous aortic valve replacement: experience with the Criber-Edwards™ percutaneous heart valve," EuroIntervention Supplements (2006), 1 (Supplement A) A3-A8.
Huber, et al., "Do Valved Stents Compromise Coronary Flow?" Eur. J. Cardiothorac. Surg. 2004;25:754-759.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. IV-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Webb, et al., "Percutaneous Aortic Valve Implantation Retrograde from the Femoral Artery," Circulation (2006), 113;842-850.
Stassano et al., "Mid-term results of the valve-on-valve technique for bioprosthetic failure," Eur. J. Cardiothorac. Surg. 2000; 18:453-457.
Pavcnik et al., "Aortic and venous valve for percutaneous insertion," Min. Invas. Ther. & Allied Techol. 2000, vol. 9, pp. 287-292.

PROSTHETIC HEART VALVE FOR TRANSFEMORAL DELIVERY

CROSS-REFERENCE TO RELATED APPLICATIONS

This application claims the benefit under 35 U.S.C. § 119(e) of U.S. patent application Ser. No. 61/192,199, filed Sep. 15, 2008, which is herein incorporated by reference in its entirety. This application is also a continuation in part of earlier filed U.S. patent application Ser. No. 12/248,776, filed Oct. 9, 2008 (the "'776 Application"), which '776 Application claimed the benefit of U.S. Provisional Application 60/978,794, filed Oct. 10, 2007, entitled, "Prosthetic heart valve specially adapted for transfemoral delivery," which is assigned to the assignee of the present application and is incorporated herein by reference.

FIELD OF THE INVENTION

The present invention relates generally to prosthetic heart valves, and specifically to prosthetic heart values configured for transfemoral delivery.

BACKGROUND OF THE INVENTION

Aortic valve replacement in patients with severe valve disease is a common surgical procedure. The replacement is conventionally performed by open heart surgery, in which the heart is usually arrested and the patient is placed on a heart bypass machine. In recent years, prosthetic heart valves have been developed which are implanted using minimally invasive procedures such as transapical or percutaneous approaches. These methods involve compressing the prosthesis radially to reduce its diameter, inserting the prosthesis into a delivery tool, such as a catheter, and advancing the delivery tool to the correct anatomical position in the heart. Once properly positioned, the prosthesis is deployed by radial expansion within the native valve annulus.

PCT Publication WO 05/002466 to Schwammenthal et al., which is assigned to the assignee of the present application and is incorporated herein by reference, describes prosthetic devices for treating aortic stenosis.

PCT Publication WO 06/070372 to Schwammenthal et. al., which is assigned to the assignee of the present application and is incorporated herein by reference, describes a prosthetic device having a single flow field therethrough, adapted for implantation in a subject, and shaped so as to define a fluid inlet and a diverging section, distal to the fluid inlet.

US Patent Application Publication 2006/0149360 to Schwammenthal et al., which is assigned to the assignee of the present application and is incorporated herein by reference, describes a prosthetic device including a valve-orifice attachment member attachable to a valve in a blood vessel and including a fluid inlet, and a diverging member that extends from the fluid inlet, the diverging member including a proximal end near the fluid inlet and a distal end distanced from the proximal end. A distal portion of the diverging member has a larger cross-sectional area for fluid flow therethrough than a proximal portion thereof.

US Patent Application Publication 2004/0236411 to Sarac et al., which is incorporated herein by reference, describes a prosthetic valve for replacing a cardiac valve, which includes an expandable support member and at least two valve leaflets made of a first layer of biological material selected from peritoneal tissue, pleural tissue or pericardial tissue. A second layer of biological material is attached to the support member. The second layer is also made from peritoneal tissue, pleural tissue or pericardial tissue. The second layer includes a radially inwardly facing surface that defines a conduit for directing blood flow. The valve leaflets extend across the conduit to permit unidirectional flow of blood through the conduit. Methods for making and implanting the prosthetic valve are also described.

US Patent Application Publication 2006/0259136 to Nguyen et al., which is incorporated herein by reference, describes a heart valve prosthesis having a self-expanding multi-level frame that supports a valve body comprising a skirt and plurality of coapting leaflets. The frame transitions between a contracted delivery configuration that enables percutaneous transluminal delivery, and an expanded deployed configuration having an asymmetric hourglass shape. The valve body skirt and leaflets are constructed so that the center of coaptation may be selected to reduce horizontal forces applied to the commissures of the valve, and to efficiently distribute and transmit forces along the leaflets and to the frame. Alternatively, the valve body may be used as a surgically implantable replacement valve prosthesis.

The following patents and patent application publications, all of which are incorporated herein by reference, may be of interest:

US Patent Application Publication 2005/0197695 to Stacchino et al.
U.S. Pat. No. 6,312,465 to Griffin et al.
U.S. Pat. No. 5,908,451 to Yeo
U.S. Pat. No. 5,344,442 to Deac
U.S. Pat. No. 5,354,330 to Hanson
US Patent Application Publication 2004/0260389 to Case et al.
U.S. Pat. No. 6,730,118 to Spencer et al.
U.S. Pat. No. 7,018,406 to Seguin et al.
U.S. Pat. No. 7,018,408 to Bailey et al.
U.S. Pat. No. 6,458,153 and US Patent Application Publication 2003/0023300 to Bailey et al.
US Patent Application Publication 2004/0186563 to Lobbi
US Patent Application Publication 2003/0130729 to Paniagua et al.
US Patent Application Publication 2004/0236411 to Sarac et al.
US Patent Application Publication 2005/0075720 to Nguyen et al.
US Patent Application Publication 2006/0056872 Salahieh et al.
US Patent Application Publication 2005/0137688 to Salahieh et al.
US Patent Application Publication 2005/0137690 to Salahieh et al.
US Patent Application Publication 2005/0137691 to Salahieh et al.
US Patent Application Publication 2005/0143809 to Salahieh et al.
US Patent Application Publication 2005/0182483 to Osborne et al.
US Patent Application Publication 2005/0137695 to Salahieh et al.
US Patent Application Publication 2005/0240200 to Bergheim
US Patent Application Publication 2006/0025857 to Bergheim et al.

US Patent Application Publication 2006/0025855 to Lashinski et al.

US Patent Application Publication 2006/0047338 to Jenson et al.

US Patent Application Publication 2006/0052867 to Revuelta et al.

US Patent Application Publication 2006/0074485 to Realyvasquez

US Patent Application Publication 2003/0149478 to Figulla et al.

U.S. Pat. No. 7,137,184 to Schreck
U.S. Pat. No. 6,296,662 to Caffey
U.S. Pat. No. 6,558,418 to Carpentier et al.
U.S. Pat. No. 7,267,686 to DiMatteo et al.

SUMMARY OF THE INVENTION

In some embodiments of the present invention, a prosthetic heart valve prosthesis comprises a collapsible support frame and a prosthetic valve. The support frame is shaped so as to define three commissural posts to which the prosthetic valve is coupled, an upstream skirt, and a plurality of downstream axial support extensions. The commissural posts are arranged circumferentially around a central longitudinal axis of the valve prosthesis, and extend in a downstream direction at a first angle with respect to the central longitudinal axis. The upstream skirt includes a plurality of cells that extend outward in an upstream direction. The skirt is configured to apply an axial force in a downstream direction on an upstream side of the native annulus and left ventricular outflow tract (LVOT).

The downstream axial support extensions join a downstream side of the skirt, and extend in a downstream direction at a second angle with respect to the central longitudinal axis, which second angle is greater than the first angle between the commissural posts and the axis. Because of this greater angle, the downstream axial support extensions (a) apply an upstream axial force to a downstream side of the native leaflet tips, (b) do not touch the leaflets of the prosthetic valve when the prosthetic valve is in its open position, (c) provides stability to the support frame.

In some embodiment of the present invention, the support frame is shaped so as to define a plurality of upper sinus support elements, which extend in a downstream direction. The upper sinus support elements are configured to rest against the upper aortic sinuses (i.e., the downstream portion of the aortic sinuses) upon implantation of the valve prosthesis, so as to provide support against tilting of the prosthesis with respect to the central longitudinal axis thereof. For some applications, the support frame is shaped so as to define exactly three downstream axial support extensions and exactly six upper sinus support elements.

In some embodiments of the present invention, a prosthetic heart valve prosthesis is provided that is similar to the prosthesis described above, except as follows. A portion of cells of the support frame of the prosthesis are shaped to define a plurality of outwardly-extending short axial support arms, which extend radially outward and upstream from the central longitudinal axis of the prosthesis. The shape of the support frame allows the valve prosthesis to be implanted such that an upstream section of the prosthesis is positioned upstream to the native annulus of the patient, while the axial support arms are protrude over the tips of the native leaflets, and collectively define an outer diameter that is greater than the diameter of the tips of the native leaflets. The axial support arms are distributed around the circumference of the frame such that, depending on the rotational orientation of the valve prosthesis, the arms engage and rest against either a native valve commissure (riding astride the commissure) or a leaflet tip, such that the valve prosthesis is anchored axially regardless of the rotational orientation of the prosthesis. The axial support arms are sized so as to not extend to the floors of the aortic sinuses. This configuration applies an axial force to the native valve complex from below and above the complex, anchoring the valve prosthesis in place, and inhibiting migration of the prosthetic valve both upstream and downstream. This configuration also allows the valve prosthesis to apply outward radial force to the native valve.

There is therefore provided, in accordance with an embodiment of the present invention, apparatus including a valve prosthesis for attachment to a native valve complex of a subject, the prosthesis including:
a prosthetic heart valve; and
a support frame, which is shaped so as to define:
two or more commissural posts, to which the prosthetic heart valve is coupled, which posts are arranged circumferentially around a central longitudinal axis of the valve prosthesis, and extend in a downstream direction at a first angle with respect to the central longitudinal axis,
a bulging upstream skirt, and
a plurality of downstream axial support extensions, which join a downstream side of the upstream skirt, which extend in a downstream direction at a second angle with respect to the central longitudinal axis, the second angle greater than the first angle, and which are configured to apply an axial force to a downstream side of native leaflet tips of the native valve complex.

In an embodiment, the support frame is shaped so as to define a plurality of upper sinus support elements, which extend in a downstream direction, and which are configured to rest against native upper aortic sinuses.

The present invention will be more fully understood from the following detailed description of embodiments thereof, taken together with the drawings, in which:

DETAILED DESCRIPTION OF EMBODIMENTS

Figure 1A:
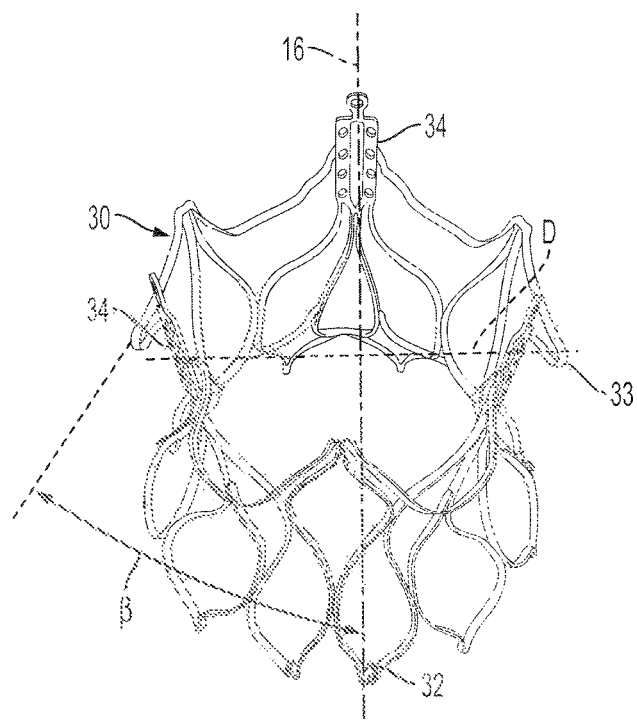
FIGS. 1A and 1B are schematic illustrations of a valve prosthesis, in accordance with an embodiment of the present invention.

FIGS. 1A and 18 are schematic illustrations of a valve prosthesis 30, in accordance with an embodiment of the present invention. FIG. 18 shows the prosthesis including a prosthetic valve 21 and a skirt 31, as described below, while FIG. 1A shows the prosthesis without these elements for clarity of illustration. Valve prosthesis 30 comprises a collapsible support frame 40, which typically comprises exactly three commissural posts 34, arranged circumferentially around a central longitudinal axis 16 of valve prosthesis 30. Valve prosthesis 30 further comprises prosthetic downstream valve 21 coupled to commissural posts 34. Valve 21 typically comprises a pliant material. The pliant material is configured to collapse inwardly (i.e., towards central longitudinal axis 16) during diastole, in order to inhibit retrograde blood flow, and to open outwardly during systole, to allow blood flow through the prosthesis.

Valve prosthesis 30 is configured to be implanted in a native diseased valve of a patient, such as a native stenotic aortic or pulmonary valve, using a minimally-invasive approach, such as a beating heart endovascular retrograde transaortic, e.g. transfemoral, procedure. Support frame 40 is typically collapsed or crimped so that its diameter is reduced in order to facilitate loading onto a catheter or cannula for delivery to the native valve site during a minimally-invasive delivery procedure, as described hereinbelow with reference to FIGS. 2, 3, and 4A-L. Support frame 40 is configured such that application of radial forces thereon radially compress the frame, reducing the frame's outer diameter. Upon removal of the radial forces, the frame assumes its earlier diameter and shape. The prosthesis, while the frame is in its compressed state, is loaded into a tube sufficiently small to allow transluminal delivery to the patient's native valve site. Support frame 40 comprises a suitable material that allows mechanical deformations associated with crimping and expansion of valve prosthesis 30, such as, but not limited to, a superelastic material, such as nitinol, or a stainless steel alloy (e.g., AISI 316).

Support frame 40 is typically shaped to define an upstream section 22, a throat section 24, and a downstream section 26. The cross-sectional area of upstream section 22 gradually decreases from an upstream end thereof to a downstream end adjacent to throat section 24. The diameter of throat section 24 is typically larger than that of the aortic annulus of the intended patient. The cross-sectional area of downstream section 26 gradually increases to an area greater than that of throat section 24. Thus the cross-sectional areas of both the upstream and downstream sections are greater than that of the throat section. Throat section 24 is configured to be placed within the leaflet section of the native valve, slightly above the aortic annulus at the ventriculo-aortic border, such that downstream section 22 is located in the aorta, such as in the aortic sinuses.

Typically, support frame is elastic, and is shaped so as to define a plurality of collapsible cells. For example, the support frame may be fabricated by cutting a solid tube. The cells may be diamond-shaped, parallelogram-shaped, or otherwise shaped to be conducive to crimping the frame. Downstream section 26 is typically shaped so as to define bulging upstream skirt 31, which is configured to apply an axial force directed toward the ascending aorta. Optionally, skirt 31 is shaped so as to define one or more barbs 32 positioned circumferentially such that the barbs pierce the native vale annulus in order to provide better anchoring. Typically, valve prosthesis 30 further comprises a skirt covering 35 which is coupled to upstream skirt 31, such as by sewing the covering within the skirt (configuration shown in FIG. 1B) or around the skirt (configuration not shown). Skirt covering 35 may comprise, for example, polyester or a processed biological material, such as pericardium. Support frame 40 thus defines a central structured body for flow passage that terminates in an upstream direction in a flared inlet (upstream skirt 31) that is configured to be seated within an LVOT immediately below an aortic annulus/aortic valve.

Figure 1B:
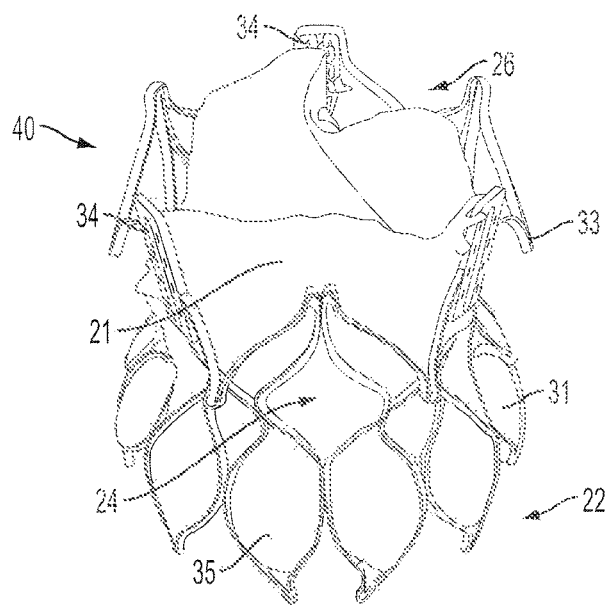

Typically, a portion of the cells of support frame 40 are shaped to define a plurality of outwardly-extending short axial support arms 33, which extend radially outward and upstream from central longitudinal axis 16. Axial support arms 33 are distributed around the circumference of the frame at a predetermined height from the upstream end of the frame, and may be either evenly (as shown in FIGS. 1A and 1B) or unevenly distributed (not shown in the figures) around the circumference. Support frame 40 typically is shaped to define at least three axial support arms 33, such as greater than three arms. For some applications, the number of support arms is a multiple of three, such as six (as shown in FIGS. 1A and 1B).

The shape of support frame 40 allows valve prosthesis 30 to be implanted such that upstream section 22 is positioned upstream to the native annulus of the patient, while axial support arms 33 protrude over the tips of the native leaflets, and collectively define an outer diameter D that is greater than the diameter of the tips of the native leaflets. Axial support arms 33 flare out laterally in an upstream direction during deployment at an angle β with central longitudinal axis 16 of valve prosthesis 30. Axial support arms 33 are radially distributed around the frame such that, depending on the rotational orientation of valve prosthesis 30, the axial support arms engage and rest against either a native valve commissure (riding astride the commissure) or a leaflet tip, such that the valve prosthesis is anchored axially regardless of the rotational orientation of the prosthesis, as described in more detail hereinbelow with reference to FIGS. 5A-C. Axial support arms 33 are sized so as to not extend to the floors of the aortic sinuses. This configuration applies an axial force to the native valve complex from below and above the complex, anchoring valve prosthesis 30 in place, and inhibiting migration of the prosthetic valve both upstream and downstream. This configuration also allows the valve prosthesis to apply outward radial force to the native valve.

Although exactly three commissural posts 34 are shown in the figures, for some applications valve prosthesis 30 comprises fewer or more posts 34, such as two posts 34, or four or more posts 34. It is noted that approximately 90% of humans have exactly three aortic sinuses. The three posts provided in most embodiments correspond to these three aortic sinuses. For implantation in the approximately 10% of patients that have exactly two aortic sinuses, prosthesis 30 typically includes exactly two posts.

Figure 2:
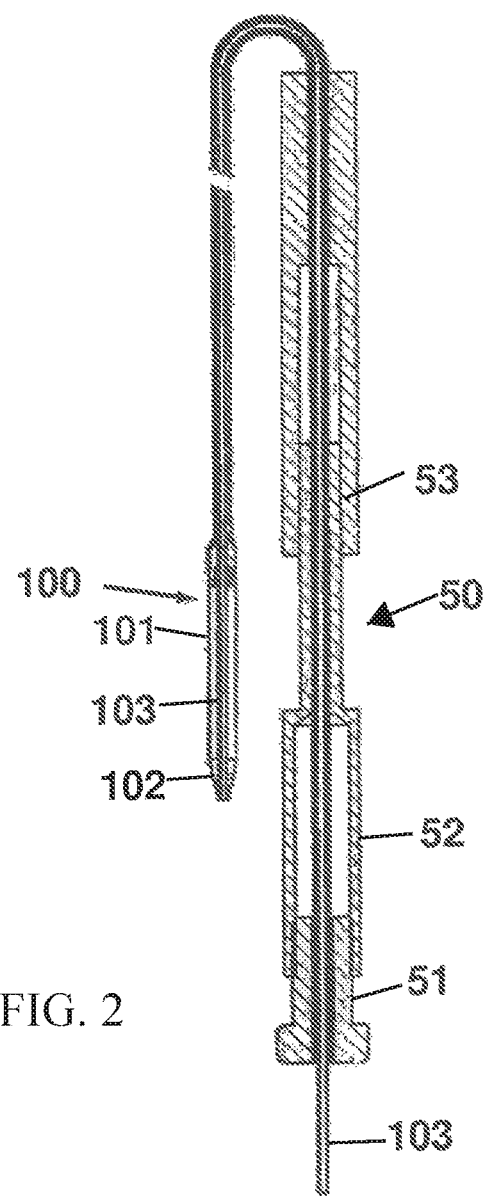
FIG. 2 is a schematic illustration of a delivery system for delivering the valve prosthesis of FIG. 1 to a target site and implanting the prosthesis at the site, in accordance with an embodiment of the present invention.

FIG. 2 is a schematic illustration of a delivery system 50 for delivering valve prosthesis 30 to a target site and implanting the prosthesis at the site, in accordance with an embodiment of the present invention. Delivery system 50 comprises a catheter 100, which comprises an inner neutral tube 103 which is concentric with an outer tube 101. The diameter of outer tube 101 typically varies along catheter 100. Neutral tube 103 is fixed with respect to neutral tube holder 51 and a handle 52. A tip 102 of catheter 100 is located at a downstream end of neutral tube 103, such that outer tube 101 abuts against tip 102 when catheter 100 is in a closed position, as shown in FIG. 2. Delivery system 50 is used to effect the release of valve prosthesis 30 (the prosthesis is not shown in FIG. 2) by moving the tubes 101 and 103 with respect to one another. Delivery system further comprises an outer tube holder 51 and a delivery body 53, which can move with respect to neutral tube holder 51 and handle 52. To open the catheter, outer tube holder 51 is pulled backwards, while handle 52 and neutral tube holder 51 are held stationary. As a result, outer tube 101 moves in a backward direction with respect to neutral tube 103, and the catheter opens. The downstream end of outer tube 101 is fixed to the upstream end of tip 102.

Figure 3:
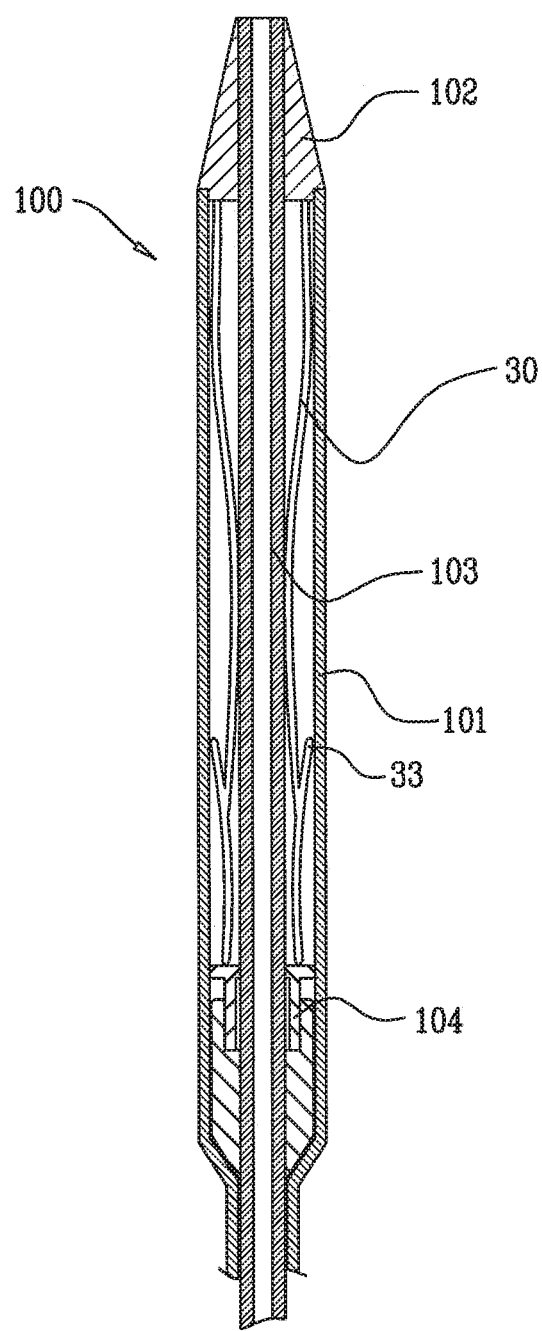
FIG. 3 is a schematic cross-sectional illustration of a front end of a catheter of the delivery system of FIG. 2, in accordance with an embodiment of the present invention.

FIG. 3 is a schematic cross-sectional illustration of a front end of catheter 100, in accordance with an embodiment of the present invention. Valve prosthesis 30 is shown within the catheter in the prosthesis's compressed state, held in a valve holder 104 and compressed between neutral tube 103 and outer tube 101. The catheter is in its closed state, such that the downstream end of outer tube 101 rests against the upstream end of tip 102.

FIGS. 4A-L schematically illustrate a procedure for implanting valve prosthesis 30 using delivery system 50, in accordance with an embodiment of the present invention. Although these figures show the implantation of the prosthesis in an aortic position, these techniques, as appropriately modified, may also be used to implant the prosthesis in other locations, such as in a pulmonary valve.

Figure 4A:
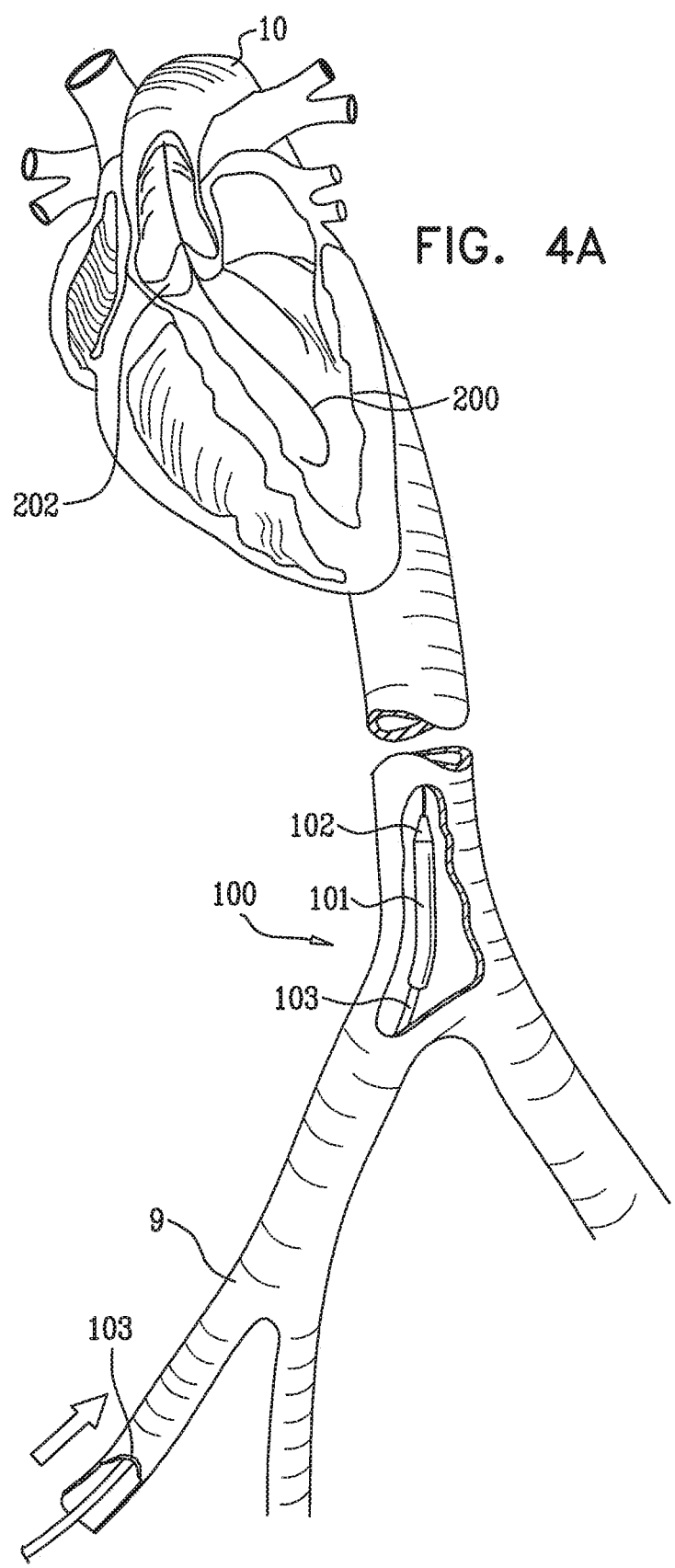
FIGS. 4A-L schematically illustrate a procedure for implanting the valve prosthesis of FIG. 1 using the delivery system of FIG. 2, in accordance with an embodiment of the present invention.

As shown in FIG. 4A, delivery catheter 100 is inserted into a body lumen 15. For some applications, body lumen 15 is a femoral artery. The catheter is inserted into body lumen 15, and is guided over a guidewire 200 through the ascending aorta and over an aortic arch 10. Optionally, stenotic aortic valve 340 is partially dilated to about 15-20 mm (e.g., about 16 mm), typically using a standard valvuloplasty balloon catheter.

Figure 4B:
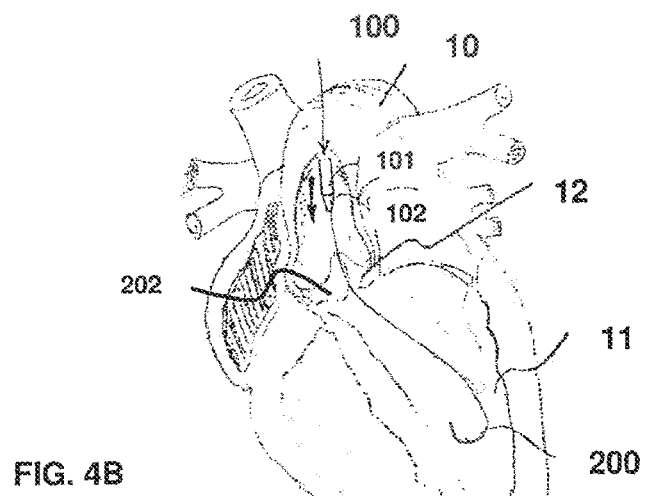

As shown in FIG. 4B, catheter 100, which rides over guidewire 200, is passed over aortic arch 10 towards a native aortic valve 202. The tip of guidewire 200 passes into a left ventricle 11.

Figure 4C:
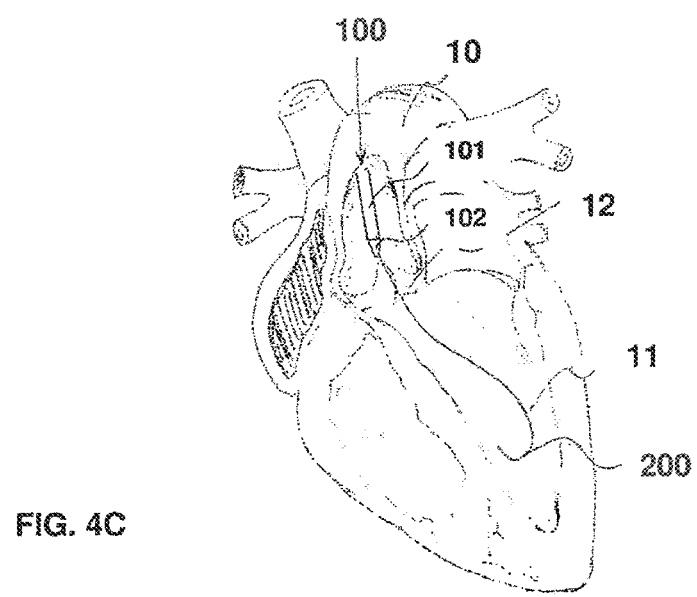

As shown in FIG. 4C, catheter tip 102 is advanced toward the junction of native aortic valve leaflets 12 towards left ventricle 11, while the catheter continues to ride over the guidewire.

Figure 4D:
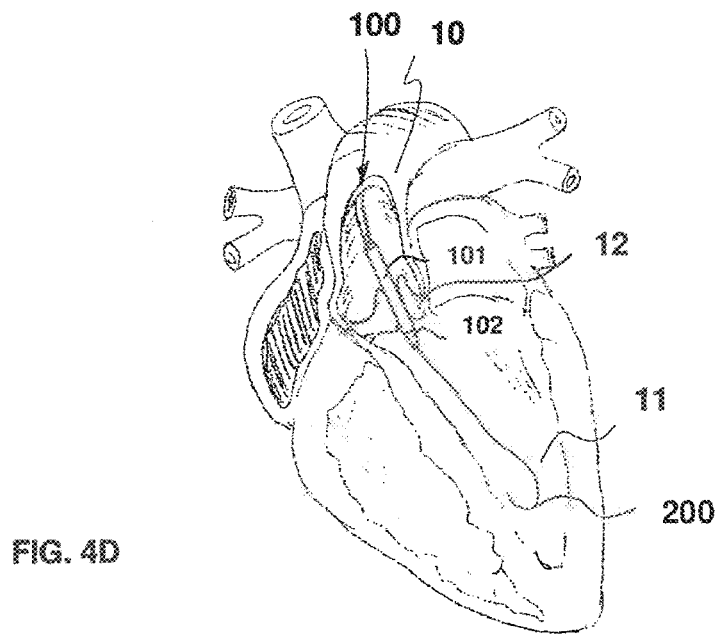

As shown in FIG. 4D, catheter tip 102 is brought past native aortic valve leaflets 12 into left ventricle 11. Outer tube 101 of catheter 100 is located between native aortic leaflets 12.

Figure 4E:
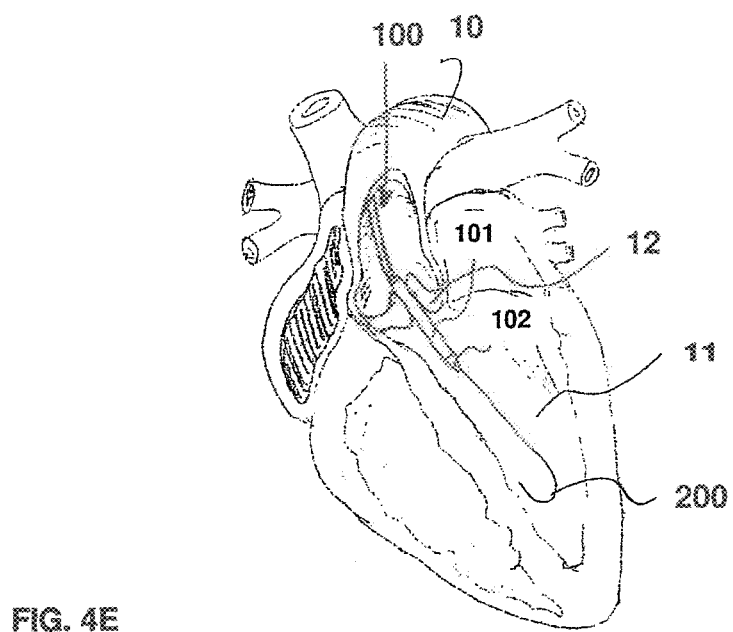

As shown in FIG. 4E, catheter tip 102 is further advanced, past aortic leaflets 12 and deeper into left ventricle 11. Outer tube 101 of catheter 100 is still located between native aortic leaflets 12.

Figure 4F:
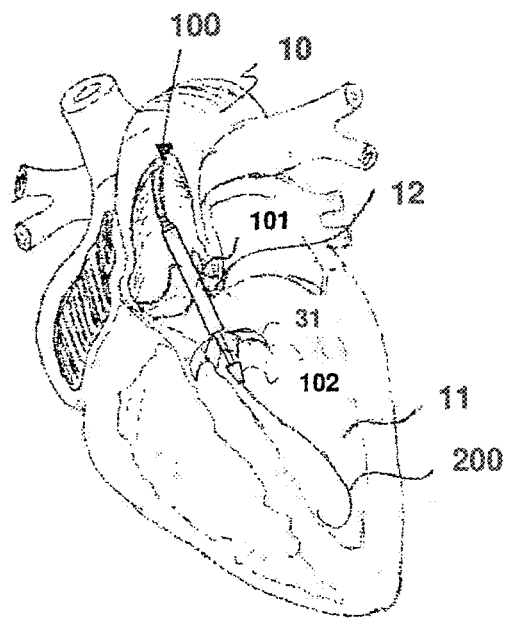

As shown in FIG. 4F, outer tube 101 is withdrawn a predetermined distance to expose upstream skirt 31 of valve prosthesis 30. Outer tube 101 moves with respect to inner tube 103, such that valve prosthesis 30 and inner tube 103 are partially exposed from the catheter. Skirt 31 is positioned within left ventricle 11. At this point during the implantation procedure, skirt 31 may not yet have come in contact with the ventricular side of native aortic leaflets 12.

Figure 4G:
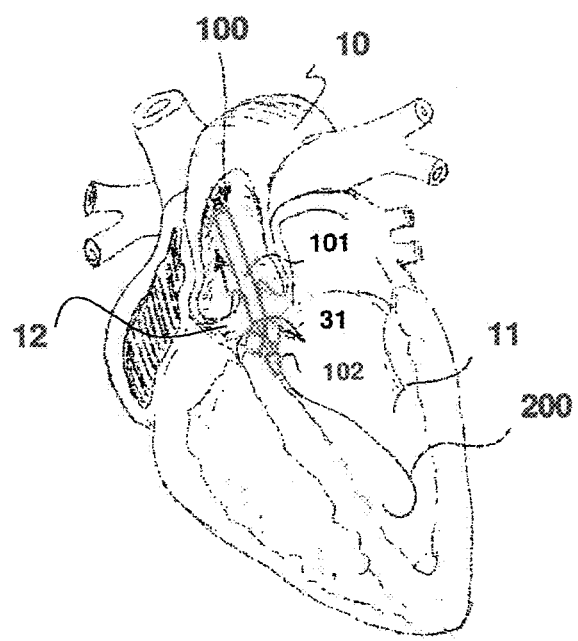
Figure 4H:
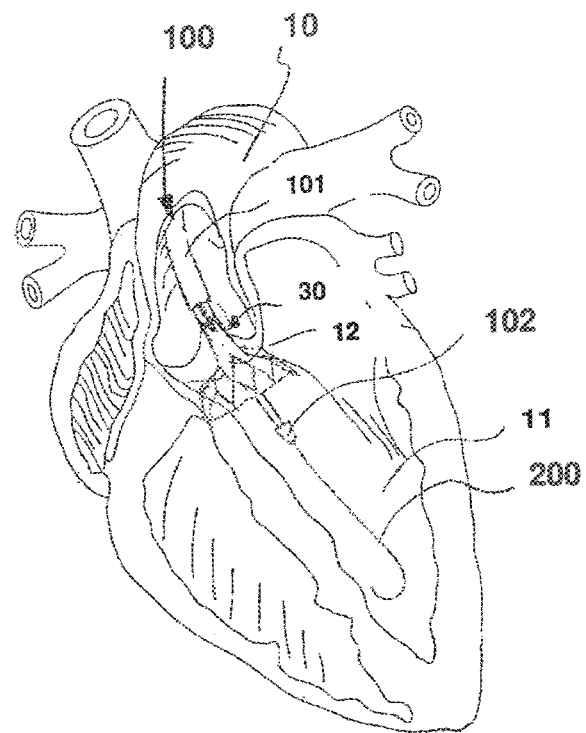

As shown in FIG. 4G, catheter 100 is withdrawn until skirt 31 abuts firmly against the ventricular side of the aortic annulus and/or aortic valve leaflets 12. If provided, barbs 32 may pierce the native annulus, or may rest against the ventricular side of the valve complex.

As shown in FIG. 4S, outer tube 101 is further withdrawn until the tube is located just upstream of the ends of commissural posts 34 of valve prosthesis 30, such that the commissural posts are still held firmly by outer tube 101.

Figure 4I:
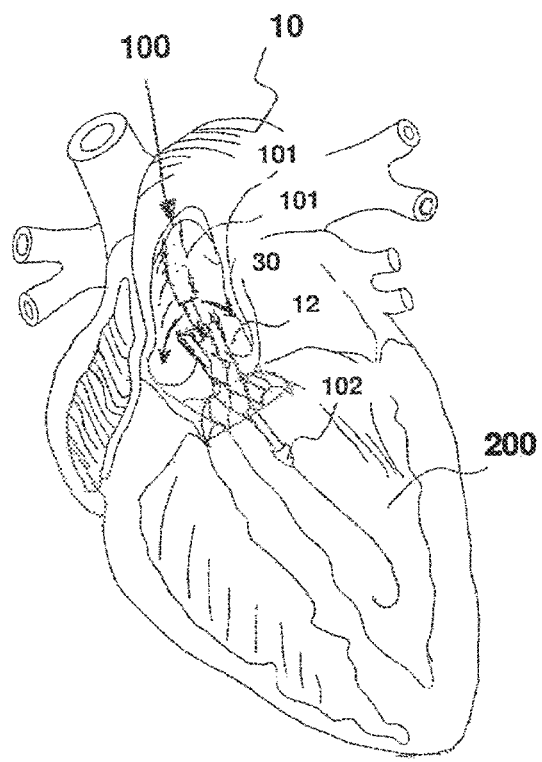

FIG. 4I shows valve prosthesis 30 immediately upon release from cuter tube 101. Support frame 40, which is typically superelastic, rapidly expands to its fully opened position, pushing native valve leaflets 12 radially outward.

Figure 4J:
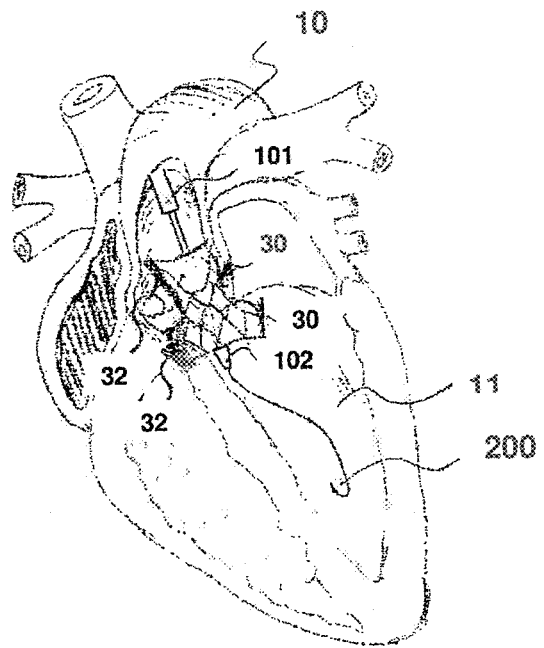

FIG. 4J shows the opening of valve prosthesis 30 to its fully expanded shape. Axial support arms 33 protrude over the tips of the native leaflets 12, so that they provide axial support to prosthetic valve 30, and prevent the valve from being forced into the ventricle 11 through native leaflets 12 during the cardiac cycle. Prosthetic valve 30 is thus released with the outer tube being moved in only one direction during the entire procedure, which facilitates the implantation procedure significantly.

Figure 4K:
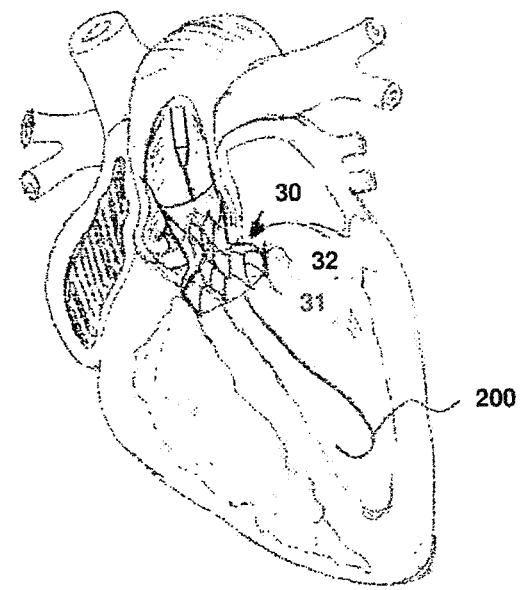

FIG. 4K shows catheter 100 in its closed position, with outer tube 101 resting firmly against catheter tip 102. Catheter 100 is withdrawn over the aortic arch, still riding on guidewire 200.

Figure 4L:
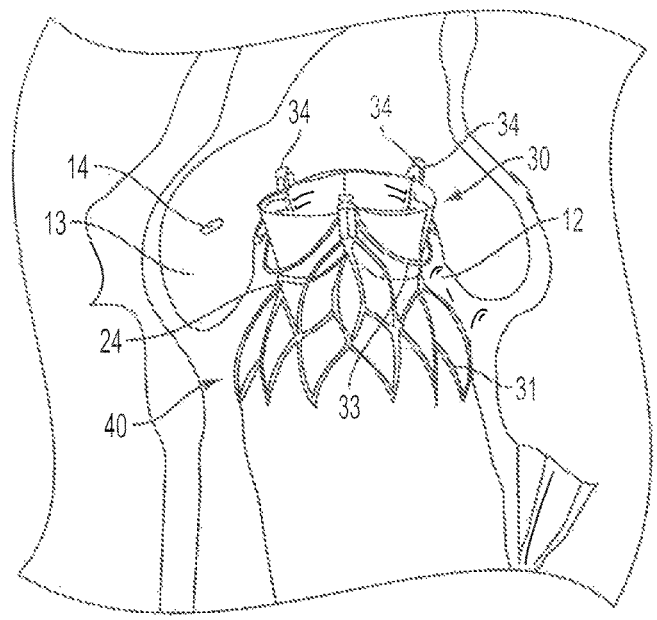

FIG. 4L is a schematic illustration of prosthetic valve 30 in the aortic position, in accordance with an embodiment of the present invention. Skirt 31 is positioned within ventricle 11 such that the throat section 24 of support frame 40 is located in close proximity to the native annulus between native leaflets 12. Commissural posts 34 of valve prosthesis 30 generally define a diverging shape, and are located on the arterial side of the native valve. Native valve leaflets 12 generally follow the contour of valve prosthesis 30. Axial support arms 33 protrude over the tips of the native leaflets, and provide axial support to prevent device embolism into ventricle 11. It is noted that in the configuration shown, valve prosthesis 30 does not include barbs 32, described hereinabove with reference to FIGS. 1A and 1B.

Figure 5A:
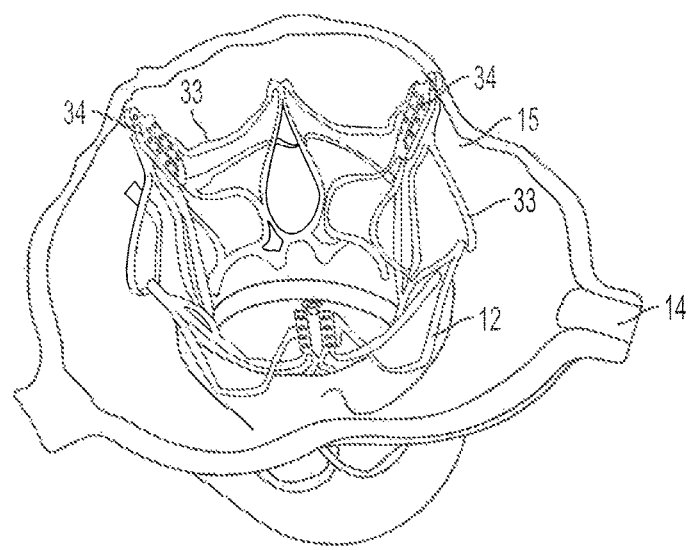
FIGS. 5A-C are schematic illustrations of three different possible rotational orientations of the valve prosthesis of FIG. 1 with respect to the native valve upon deployment, in accordance with an embodiment of the present invention.
Figure 5B:
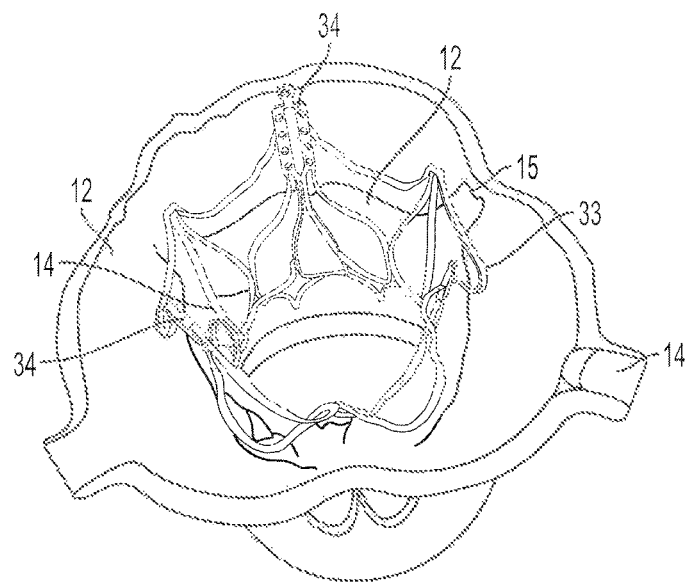
Figure 5C:
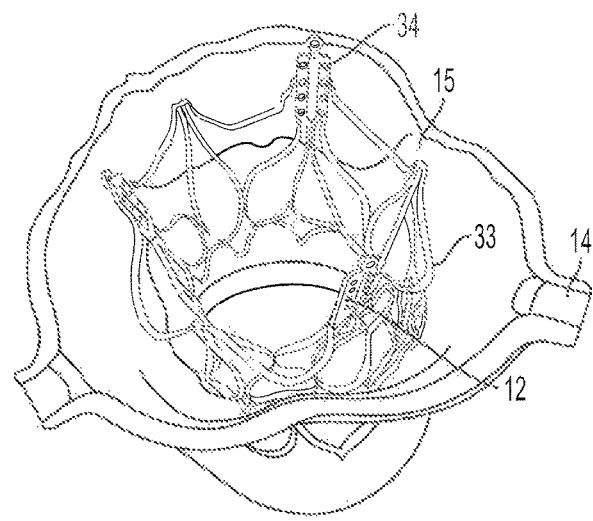

FIGS. 5A-C are schematic illustrations of three different possible rotational orientations of valve prosthesis 30 with respect to the native valve upon deployment, in accordance with an embodiment of the present invention. All of these rotational orientations, as well as intermediate rotational orientations not shown, provide proper axial fixation of the valve prosthesis. For clarity of illustration, in FIGS. 5A-C only support frame 40 of the valve prosthesis is shown, without prosthetic downstream valve 21 or skirt covering 35 of skirt 31. The valve prosthesis is deployed within the aortic root, which includes aortic sinuses, coronary ostia 14, and native valve commissures 15. Upon implantation, valve prosthesis 30 provides axial anchoring on both sides (ventricular and arterial) of the native valve annulus. Skirt 31 extends radially below the annulus, providing an axial force applied in the arterial direction to the underside of the annulus, while axial support arms 33 exert an axial force in the ventricular direction by resting against the tips of native leaflets 12 or native commissures 15.

FIG. 5A shows a first possible rotational orientation of valve prosthesis 30, in which commissural posts 34 of the prosthesis are aligned with native commissures 15, allowing axial support arms 33 to rest against the tips of native leaflets 12.

FIG. 5B shows another possible rotational orientation of prosthetic valve 30 within the native valve complex, in which commissural posts 34 of the prosthesis are positioned at a rotational offset of about 60 degrees with respect to native commissures 15, with axial support arms 33 extending over the tips of native leaflets 12. As can be seen in FIG. 5B, axial support arms 33 provide axial anchoring, regardless of the rotational orientation of the prosthesis with respect to the native valve. As can be seen, axial support arms 33, which are circumferentially distributed around prosthetic valve 30, obviate the need to rotationally align prosthetic valve 30 with any anatomical feature of the native valve complex, since axial support arms 33 are generally guaranteed to be located between native commissures 15, or riding astride the native commissures 15.

FIG. 5C shows yet another possible rotational orientation of prosthetic valve 30 within the native valve complex upon deployment, in which commissural posts 34 of the prosthesis are offset with respect to native valve commissures 15 by about 30 degrees. Even in this particular rotationally asymmetric position, axial support arms 33 engage the tips of native leaflets 12, or native valve commissures 15, effectively applying a downward axial force to the native structure, obviating the need for deliberate rotational positioning of prosthetic valve 30 during the implantation process.

For some applications, prosthesis 30 is implanted using some of the techniques described with reference to FIGS. 9A-G in U.S. application Ser. No. 12/050,628, filed Mar. 18, 2008, entitled, "Valve suturing and implantation procedures," which is incorporated herein by reference.

Figures 6A, 6B:
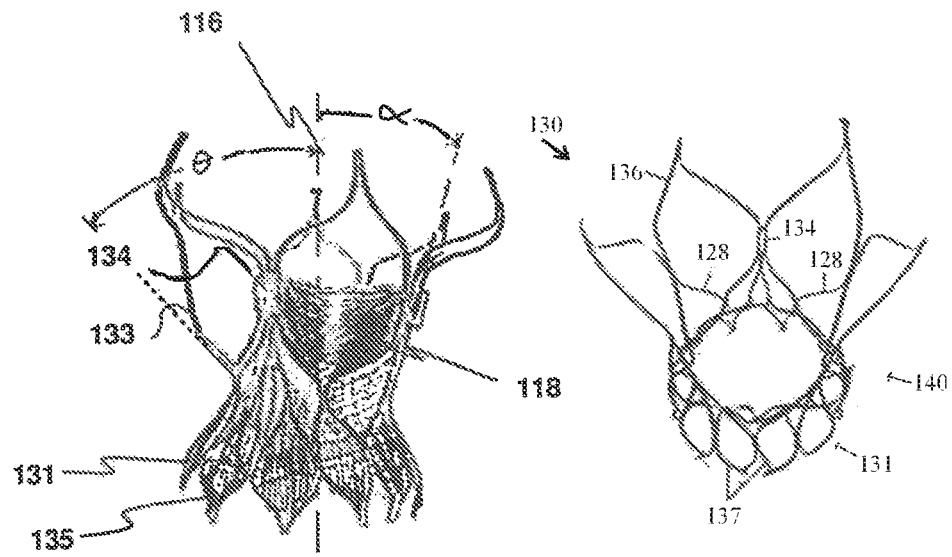
FIGS. 6A-D are schematic illustration of another valve prosthesis, in accordance with an embodiment of the present invention.
Figures 6C, 6D:
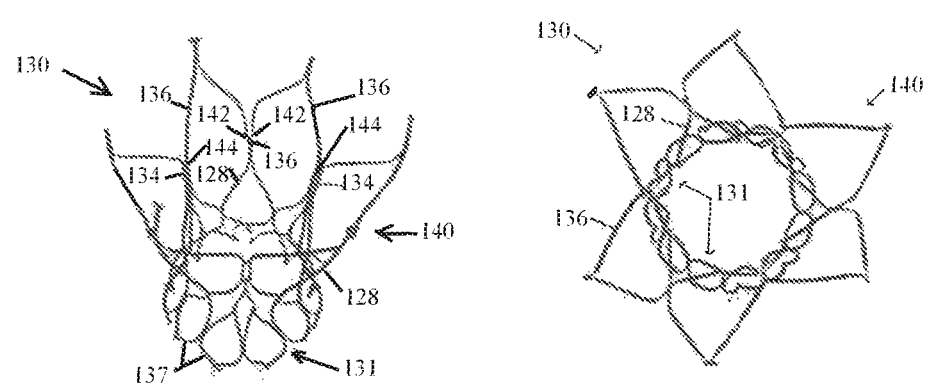

Reference is now made to FIGS. 6A-D, which are schematic illustration of a valve prosthesis 130, in accordance with an embodiment of the present invention. FIG. 6A shows the prosthesis including a prosthetic downstream valve 118 and a skirt covering 135 of a skirt 131, while FIGS. 6B, 6C, and 6D, for clarity of illustration, shows only a support frame 140 of the valve prosthesis, without prosthetic downstream valve 118 or skirt covering 135 of skirt 131. FIGS. 6A-C are side views, while FIG. 6D is a top view of the valve prosthesis (viewed from the downstream side). Skirt covering 135 may comprise, for example, polyester or a processed biological material, such as pericardium.

Other than as described hereinbelow, valve prosthesis 130 is generally similar to valve prosthesis 30, described hereinabove with reference to FIGS. 1, 4A-L, and 5A-C. For example, as described hereinabove with respect to valve prosthesis 30, valve prosthesis 130 comprises support frame 140, which is shaped so as to define three commissural posts 134 to which prosthetic valve 118 is coupled, and upstream skirt 131. The commissural posts are arranged circumferentially around a central longitudinal axis 116 of the valve prosthesis. The upstream skirt includes a plurality of cells 137 that extend outward in an upstream direction. The skirt is configured to apply an axial force in a downstream direction on an upstream side of the native annulus and left ventricular outflow tract (LVOT). Unlike valve prosthesis 30, valve prosthesis 130 typically does not comprise short axial support arms 33.

Support frame 140 is shaped so as to define a plurality of downstream axial support extensions 128. The downstream axial support extensions join a downstream side of upstream skirt 131, and extend in a downstream direction at an angle ø with respect to central longitudinal axis 116 of valve prosthesis 130, while commissural posts 134 extend in a downstream direction at an angle α with respect to axis 116 (the angles are shown in FIG. 6A). Angle ø is greater than angle α. Because of this greater angle, downstream axial support extensions 128: (a) apply an upstream axial force to a downstream side of the native leaflet tips, (b) do not touch the leaflets of the prosthetic valve when the prosthetic valve is in its open position, and (c) provide stability to support frame 140. Angle ø may, for example, be between about 15 and about 45 degrees, such as about 30 degrees, while angle α may, for example, be between about 1 and about 15 degrees, such as about 8 decrees.

For some applications, an upstream-most portion of each downstream axial support extension 128 joins the downstream site of upstream skirt 131, and two lateral portions of each extension join respective cells of the frame that extend in an upstream direction from respective commissural posts 134.

In an embodiment of the present invention, support frame 140 is shaped so as to define a plurality of upper sinus support elements 136, which extend in a downstream direction. Upper sinus support elements 136 are configured to rest against the upper aortic sinuses (i.e., the downstream portion of aortic sinuses 13) upon implantation of valve prosthesis 130, so as to provide support against tilting of the prosthesis with respect to central longitudinal axis 16 thereof. Typically, the downstream-most portions of upper sinus support elements 136 are bent toward central longitudinal axis 16 of the prosthesis to avoid damage to the walls of the upper sinuses. For some applications, support frame 140 is shaped so as to define exactly three downstream axial support extensions 128 and exactly six upper sinus support elements 136.

For some applications, as seen clearly in FIG. 6C, each upper sinus support element 136 has two upstream-most portions 142 and 144. Upstream-most portion 142 joins a downstream-most portion 146 of one of downstream axial support extensions 128, and upstream-most portion 144 joins one of commissural posts 134. For some applications, as shown in FIG. 6C, upstream-most portions 142 of two of upper sinus support elements 136 join a single downstream-most portion 146 of one of downstream axial support extensions 128, such that two of upper sinus support elements 136 are circumferentially positioned between each pair of two of commissural posts 134.

Figures 7A, 7B:
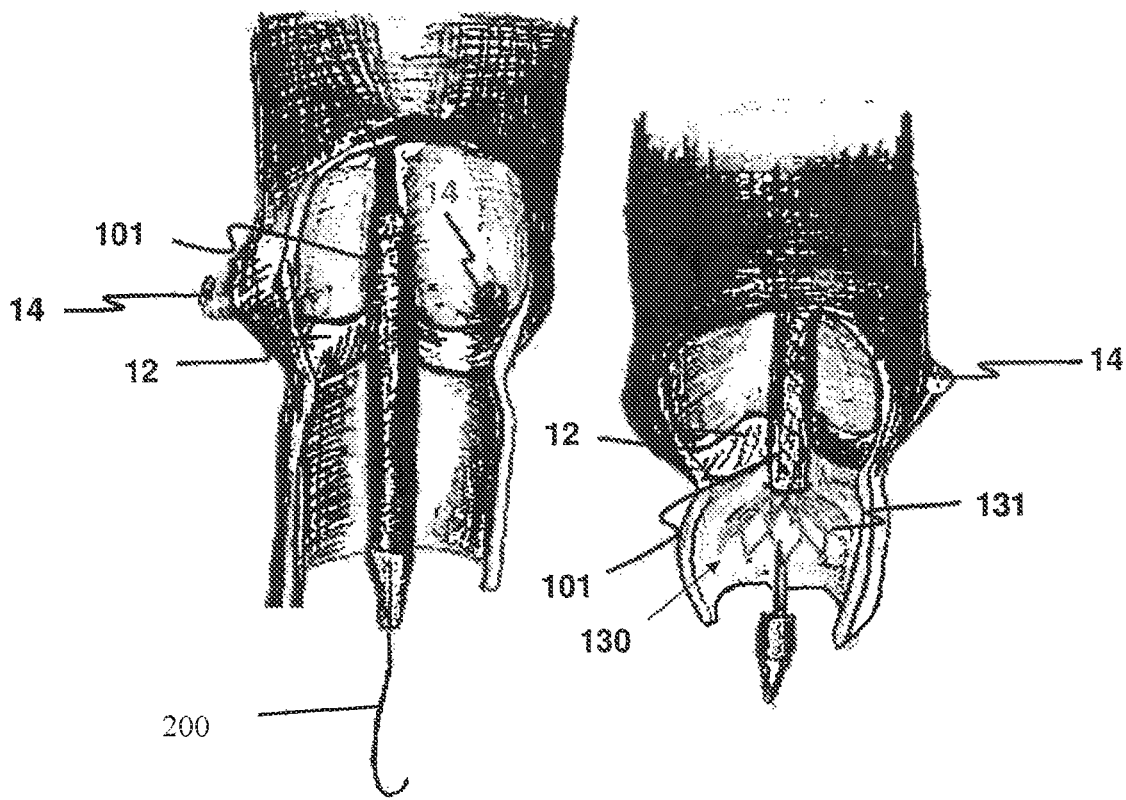
FIGS. 7A-D schematically illustrate a portion of a procedure for implanting the valve prosthesis of FIGS. 6A-C using the delivery system of FIG. 2, in accordance with an embodiment of the present invention.

FIGS. 7A-D schematically illustrate a portion of a procedure for implanting valve prosthesis 130, configured as described hereinabove with reference to FIGS. 6A-D, using delivery system 50, in accordance with an embodiment of the present invention. The first steps of the procedure are performed as described hereinabove with reference to FIGS. 4A-G, until skirt 131 abuts firmly against the ventricular side of the aortic annulus and/or aortic valve leaflets 12. After these steps, outer tube 101 is further withdrawn until the tube is located just upstream of the ends of commissural posts 134 of valve prosthesis 130, as shown in FIG. 7B. The commissural posts are still held firmly by outer tube 101.

Figure 7C:
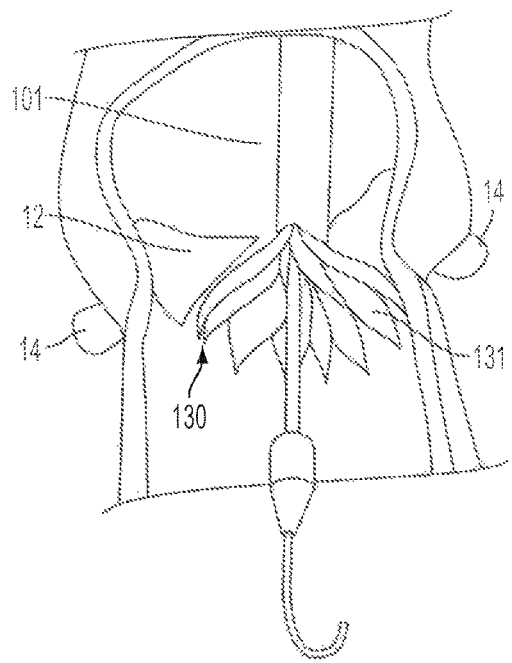

The physician performing the procedure withdraws the delivery system until he or she feels significant resistance as skirt 131 comes in contact with the upstream side of the native annulus and/or the LVOT, as shown in FIG. 7C.

Figure 7D:
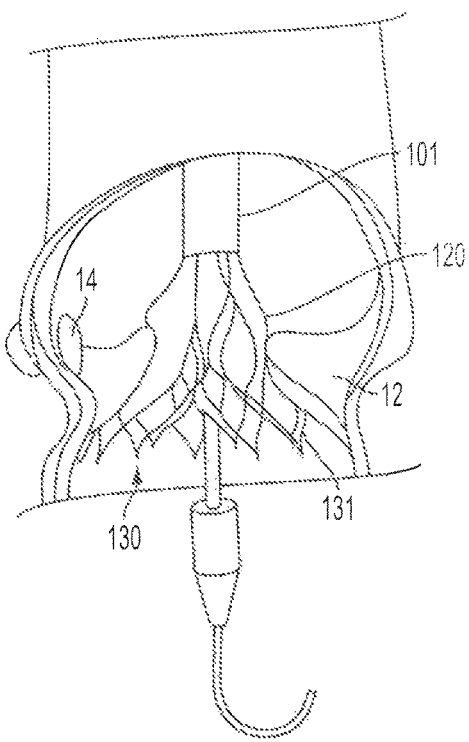

As shown in FIG. 7D, support frame 140 is gently further deployed further until bulges 120 defined by downstream axial support extensions 128 on the side of the prosthesis snap above the native leaflets, providing tactile feedback that the correct anatomical location has been reached. The prosthesis is now completely released from outer tube 101.

Figure 8A:
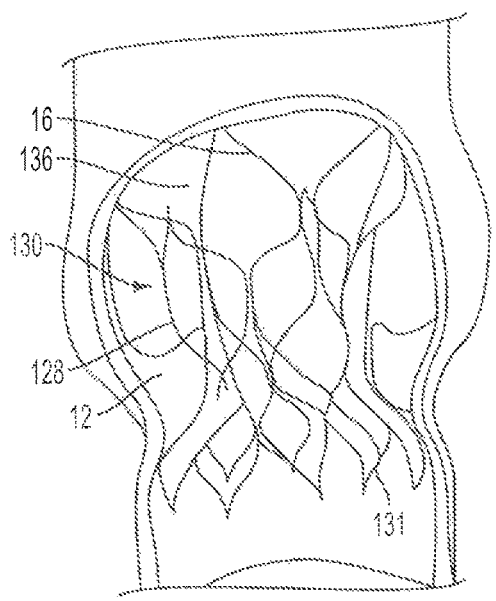
FIGS. 8A-C show the valve prosthesis of FIGS. 6A-D in place within the native aortic valve of the patient, in accordance with an embodiment of the present invention.
Figure 8B:
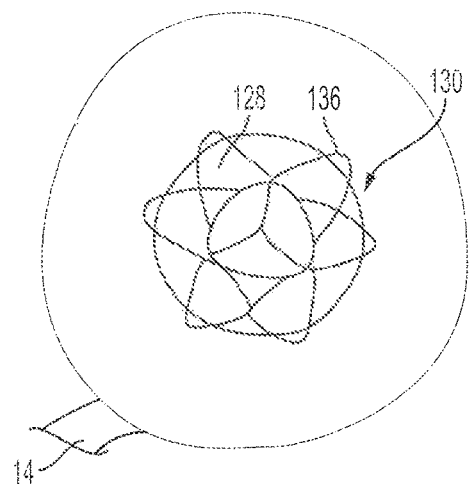
Figure 8C:
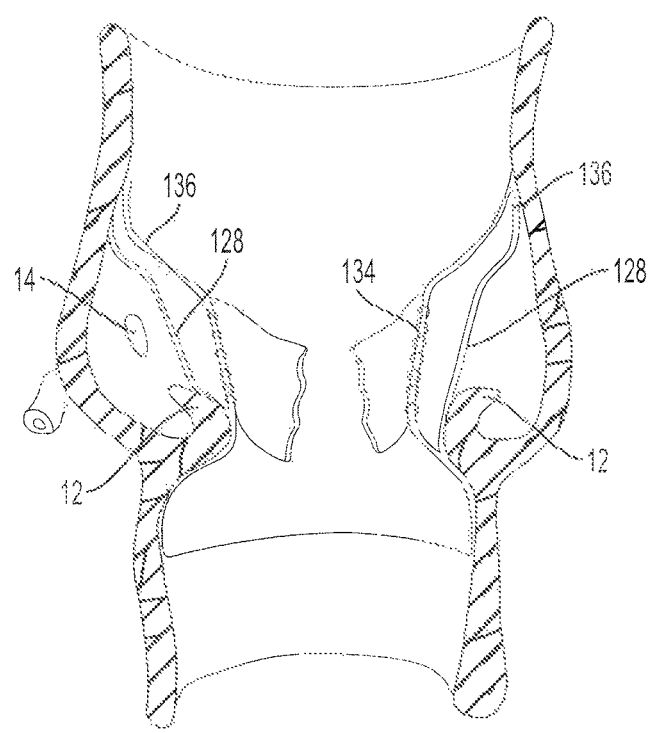

FIGS. 8A-C show valve prosthesis 130 in place within the native aortic valve of the patient, in accordance with an embodiment of the present invention. FIGS. 8A and 8C are side views, and FIG. 8B is a top view of the valve prosthesis (viewed from the downstream side). Commissural posts 134 and downstream axial support extensions 128 may or may not touch the walls of the sinuses. Typically, the downstream-most portions of upper sinus support elements 136 are bent toward central longitudinal axis 16 of the prosthesis to avoid damage to the walls of the upper sinuses.

Figure 9:
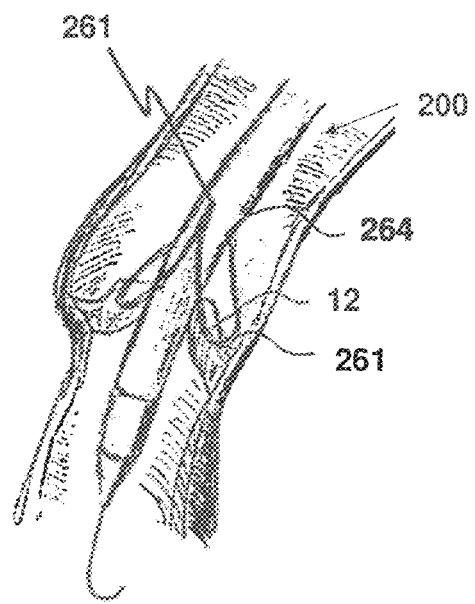
FIG. 9 is a schematic illustration of a catheter tube, in accordance with an embodiment of the present invention.

FIG. 9 is a schematic illustration of a catheter tube 200, in accordance with an embodiment of the present invention. Catheter tube 200 comprises feelers 261 which align themselves with the sinuses, thereby guiding the delivery catheter in both radial and axial directions. Feelers 261 are initially located within an outer tube 264, and extend out through slits 262 defined by the outer tube. Slits 262 may be arrange circumferentially around the catheter tube. Feelers 261 may be extended and retracted by the physician, so that the feelers are in a retracted position while the catheter is advanced through the vasculature, and are extended before the delicate placement stage of the implantation procedure.

Figure 10:
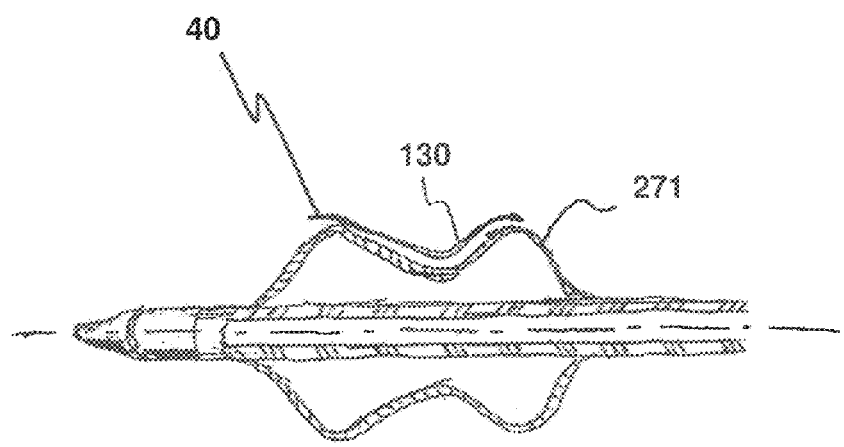
FIG. 10 is a schematic illustration of a shaped balloon, in accordance with an embodiment of the present invention.

FIG. 10 is a schematic illustration of a shaped balloon 271, in accordance with an embodiment of the present invention. The balloon is used to plastically deform support structure 40 of valve prosthesis 30 or 130, and to give the structure a non-cylindrical shape. In this embodiment, support structure 40 or 140 may comprise a stainless steel alloy which is plastically deformed during crimping, thereby reducing the valve diameter, and mounted onto the balloon prior to implantation. When the delivery catheter is in place in the patient, shaped balloon 271 is used to open the crimped prosthesis into place, and to give it a non-cylindrical shape.

In the present patent application, including in the claims, the word "downstream" means near or toward the direction in which the blood flow is moving, and "upstream" means the opposite direction. For embodiments in which the valve prosthesis is implanted at the aortic valve, the aorta is downstream and the ventricle is upstream. As used in the present patent application, including in the claims, the "native valve complex" includes the native semilunar valve leaflets, the annulus of the valve, the subvalvular tissue on the ventricular side, and the lower half of the semilunar sinuses. As used in the present application, including in the claims, a "native semilunar valve" is to be understood as including: (a) native semilunar valves that include their native leaflets, and (b) native semilunar valves, the native leaflets of which have been surgically excised or are otherwise absent.

For some applications, techniques described herein are performed in combination with techniques described in a US provisional patent application filed on even date herewith, entitled, "Prosthetic heart valve having identifiers for aiding in radiographic positioning," which is assigned to the assignee of the present application and is incorporated herein by reference.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. patent application Ser. No. 11/024,908, filed Dec. 30, 2004, entitled, "Fluid flow prosthetic device," which issued as U.S. Pat. No. 7,201,772;

International Patent Application PCT/IL2005/001399, filed Dec. 29, 2005, entitled, "Fluid flow prosthetic device," which published as PCT Publication WO 06/070372;

International Patent Application PCT/IL2004/000601, filed Jul. 6, 2004, entitled, "Implantable prosthetic devices particularly for transarterial delivery in the treatment of aortic stenosis, and methods of implanting such devices," which published as PCT Publication WO 05/002466, and U.S. patent application Ser. No. 10/563,384, filed Apr. 20, 2006, in the national stage thereof, which published as US Patent Application Publication 2006/0259134;

U.S. Provisional Application 60/845,728, filed Sep. 19, 2006, entitled, "Fixation member for valve";

U.S. Provisional Application 60/852,435, filed. Oct. 16, 2006, entitled, "Transapical delivery system with ventriculo-arterial overflow bypass";

U.S. application Ser. No. 11/728,253, filed Mar. 23, 2007, entitled, "Valve prosthesis fixation techniques using sandwiching";

International Patent Application PCT/IL2007/001237, filed Oct. 16, 2007, entitled, "Transapical delivery system with ventriculo-arterial overflow bypass," which published as PCT Publication WO 2008/047354; and/or U.S. application Ser. No. 12/050,628, filed Mar. 18, 2008, entitled, "Valve suturing and implantation procedures."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a valve prosthesis for attachment to a native valve complex of a subject, the valve prosthesis comprising:
    a prosthetic heart valve including a plurality of prosthetic leaflets; and
    a support frame, which is shaped so as to define:
        two or more commissural posts, wherein adjacent prosthetic leaflets of the plurality of prosthetic leaflets of the prosthetic heart valve are attached to each commissural post such that two prosthetic leaflets of the plurality of prosthetic leaflets are attached to each commissural post, wherein the commissural posts are arranged circumferentially around a central longitudinal axis of the valve prosthesis, and wherein each of the commissural posts extends in a downstream direction at a first radially outward angle with respect to the central longitudinal axis,
        a bulging upstream skirt disposed upstream of the two or more commissural posts, and
        a plurality of axial support extensions, an upstream end of each of the plurality of axial support extensions joined to a downstream side of the upstream skirt and a downstream end of at least some of the plurality of axial support extensions joined to upstream ends of the two or more commissural posts, wherein each axial support extension extends in a downstream direction at a second radially outward angle with respect to the central longitudinal axis, the second radially outward angle being greater than the first radially outward angle, and wherein the axial support extensions are configured to apply an axial force in an upstream direction to leaflets of the native valve complex.

2. The apparatus according to claim 1, wherein the support frame is shaped so as to define a plurality of upper sinus support elements, which extend in a downstream direction such that downstream ends of the upper sinus support elements are downstream of downstream ends of the two or more commissural posts, the upper sinus support elements being configured to rest against native upper aortic sinuses.

3. The apparatus according to claim 1, wherein the first radial outward angle is between about 1 and about 15 degrees.

4. The apparatus according to claim 1, wherein the second radial outward angle is between about 15 and about 45 degrees.

5. The apparatus according to claim 2, wherein each upper sinus support element joins a respective one of the downstream axial support extensions.

6. The apparatus according to claim 2, wherein each upper sinus support element joins a respective one of the two or more commissural posts.

7. The apparatus according to claim 2, wherein each upper sinus support element is bent radially inward toward the central longitudinal axis.

8. The apparatus according to claim 2, wherein each upper sinus support element comprises a first upstream-most portion and a second upstream-most portion,
   wherein the first upstream-most portion of a first upper sinus support element of the plurality of upper sinus support elements joins a first axial support extension of the plurality of axial support extensions,
   wherein the second upstream-most portion of the first upper sinus support element joins a first commissural post of the two or more commissural posts,
   wherein the first upstream-most portion of a second upper sinus support element of the plurality of upper sinus support elements joins the first axial support extension, and
   wherein the second upstream-most portion of a third upper sinus support of the plurality of upper sinus support elements joins the first commissural post.

9. The apparatus according to claim 1, wherein the bulging upstream skirt comprises a plurality of cells.

* * * * *